United States Patent [19]

Fritts et al.

[11] 4,379,410

[45] Apr. 12, 1983

[54] BATTERY ELECTRODE FATIGUE SIMULATOR

[75] Inventors: David H. Fritts, Dayton; John F. Leonard, Xenia, both of Ohio

[73] Assignee: The United States of America as represented by the Secretary of the Air Force, Washington, D.C.

[21] Appl. No.: 227,565

[22] Filed: Jan. 22, 1981

[51] Int. Cl.$^3$ .......................... G01N 3/32; G01N 3/08
[52] U.S. Cl. ....................................... 73/809; 73/812; 73/826; 73/808
[58] Field of Search ................ 73/808, 809, 810, 812, 73/813, 843, 893, 826, 828, 829, 830

[56] References Cited

U.S. PATENT DOCUMENTS

| | | | |
|---|---|---|---|
| 1,499,546 | 7/1924 | Okley | 73/809 |
| 3,062,044 | 11/1962 | Johnson et al. | 73/808 |
| 3,504,536 | 4/1970 | Baker et al. | 73/828 |
| 3,781,657 | 12/1973 | Dennstedt | 324/29.5 |
| 3,940,679 | 2/1976 | Brandwein et al. | 320/48 |
| 4,109,516 | 8/1978 | Fuxa | 73/843 X |
| 4,114,083 | 9/1978 | Benham et al. | 320/39 |
| 4,203,103 | 5/1980 | Osada et al. | 340/753 |

FOREIGN PATENT DOCUMENTS

1953455 3/1971 Fed. Rep. of Germany ........ 73/808

OTHER PUBLICATIONS

Tensile Fatigue Machine for Testing Wires and Single Crystals, by R. A. Dodd published in Notes about 1960, p. 69.

Fritts, David H., "Power Sources 7," J. Thompson, Ed., Academic Press, N.Y., (1979) Chapter 7.

Fritts, David H., "Some Fatigue Characteristics of Nickel Battery Plaque," AFAPL—TR—78-37, Jul. 1978.

Primary Examiner—Anthony V. Ciarlante
Assistant Examiner—David V. Carlson
Attorney, Agent, or Firm—Donald J. Singer; Jacob N. Erlich

[57] ABSTRACT

A battery electrode fatigue simulator having a frame which supports therein a pivotal and a stationary beam. The pivotal and stationary beams secure therebetween an electrode plaque which is to undergo the fatigue simulation. Also mounted to the frame is a rotatable cam of predetermined dimension which acts upon a cam follower forming part of the pivotal beam thereby causing cyclic movement or displacement of the pivotal beam. This cyclic displacement is transferred to the plaque as a cyclic stress in tension. Measurements are made of the displacement of the pivotal beam as well as resistance of the plaque during the application of the cyclic stress. The cyclic displacement versus resistance relationship is representative of the fatigue a battery electrode will undergo during actual battery operation.

6 Claims, 3 Drawing Figures

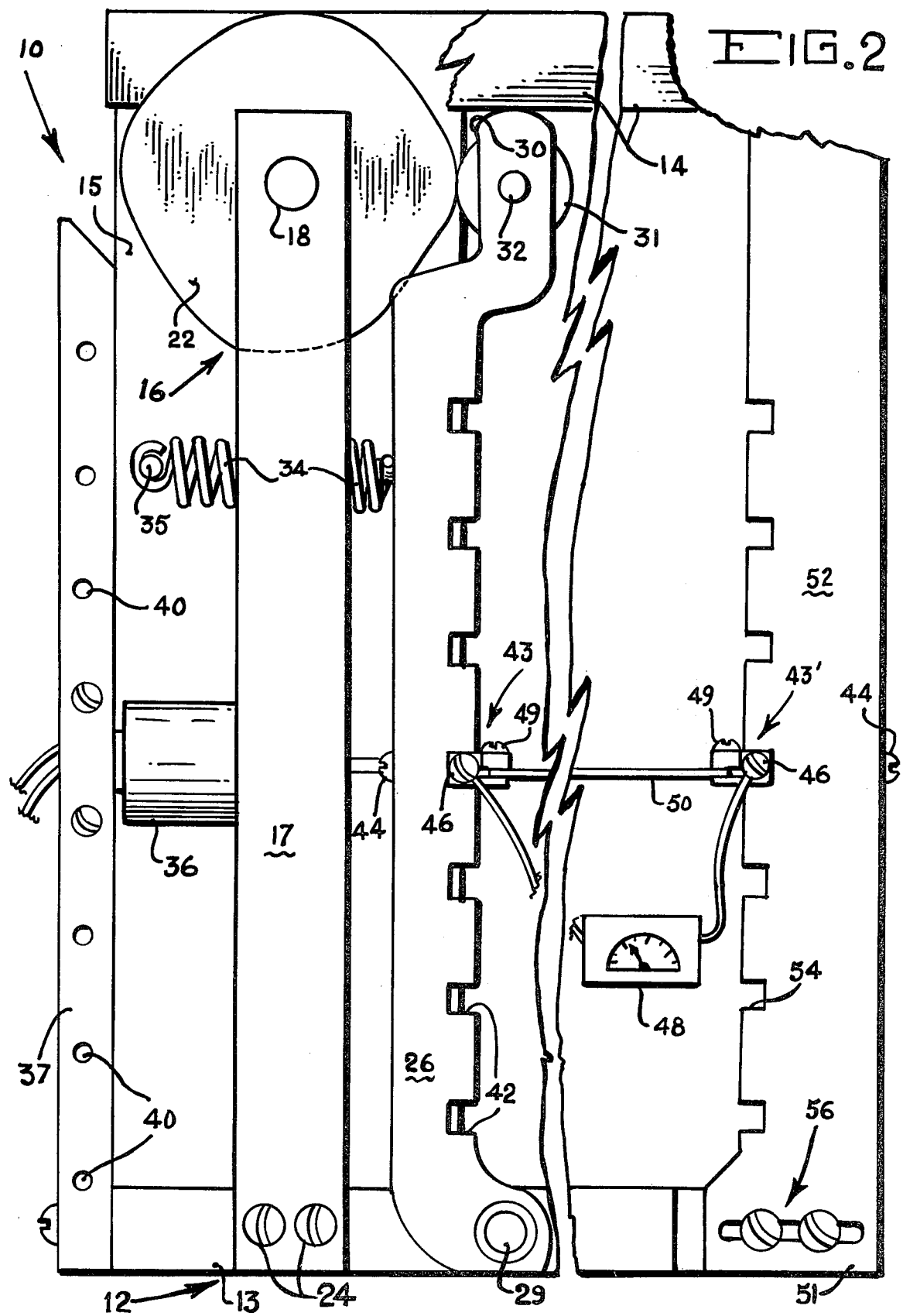

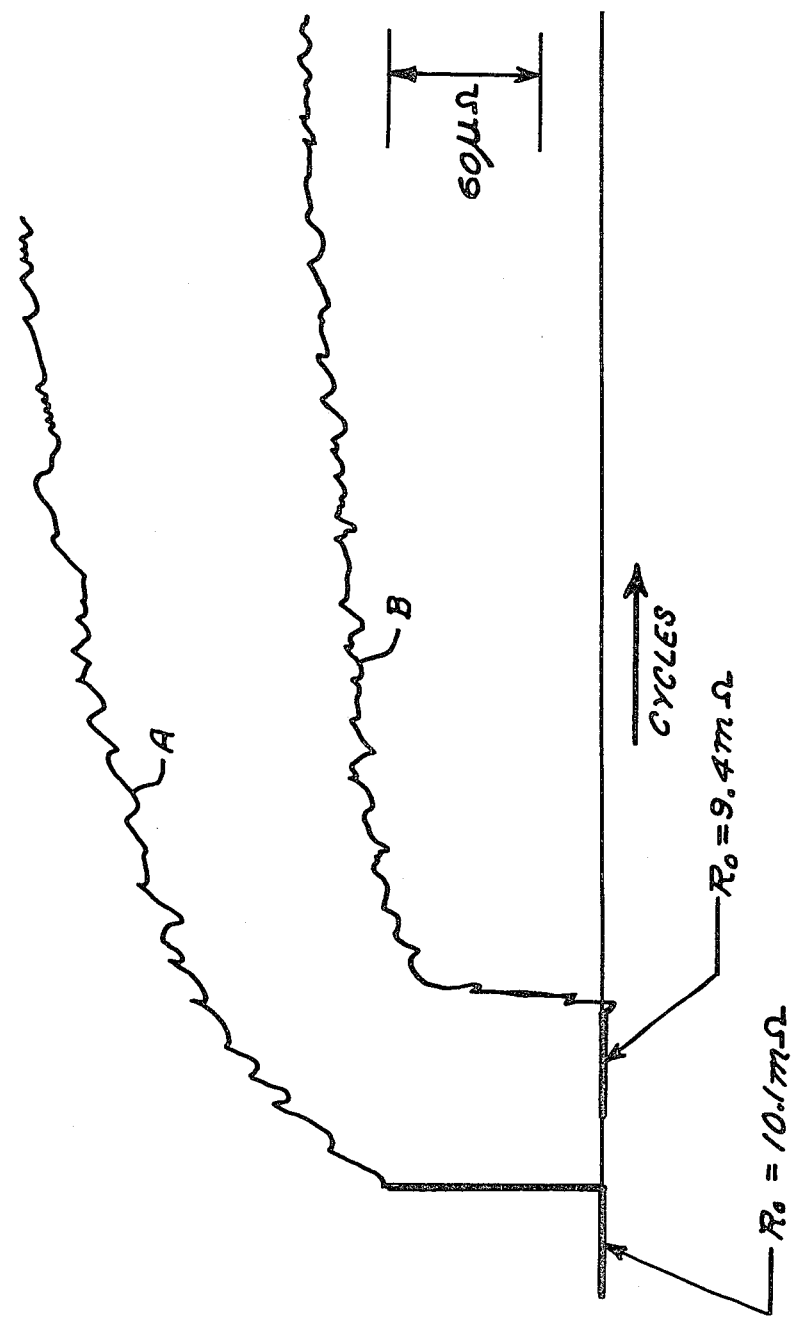

BATTERY ELECTRODE FATIGUE SIMULATOR

STATEMENT OF GOVERNMENT INTEREST

The invention described herein may be manufactured and used by or for the Government for governmental purposes without the payment of any royalty thereon.

BACKGROUND OF THE INVENTION

This invention relates generally to fatigue simulators, and more particularly, to a device which is capable of mechanically simulating the cyclic stress or fatigue which is undergone by nickel battery electrodes or more specifically, electrode plaque during battery operation.

Currently, more and more emphasis is being placed upon to the development of high performance, compact, lightweight miniaturized power sources. Such power sources generally are in the form of high quality, nickel-cadmium, nickel-zinc, and nickel-hydrogen cells or batteries. Such batteries have many applications, although their primary application is in use as an aircraft emergency power source and/or spacecraft power source.

Historically, however, there has been little interest in the mechanical characteristics of the sintered battery electrode substrate material, more commonly referred to as electrode plaque or simply by the term plaque. This substrate (plaque) has been characterized primarily in terms of its chemical compatibility, porosity, current carrying capability, and surface area. Plaque has commonly been viewed as merely an immobile and inert "container" for the active chemical components or chemically active electrode material.

Recently attention has been given to the fatique characteristics of the electrode plaque as fatigue has been shown to result in long term capacity degradation of nickel electrodes. More specifically, a primary irreversible failure mechanism of nickel electrodes is the mechanical fatigue of the plaque. The fatigue failure is a result of cyclic mechanical stresses acting on the electrode plaque and which are directly related to the number of charge-discharge cycles of a battery. The implication of this conclusion is that an improved cycle life can be obtained from nickel electrodes by building a fatigue-resistant plaque. This is particularly important in the Ni-H$_2$ battery in which the life-limiting component of the battery is the nickel electrode. Consequently, the plaque configuration and mechanical properties must be engineered to obtain maximum efficiency and life from the nickel electrode.

Currently available fatigue or stress testing equipment is inadequate for electrode plaque testing. For example, fatigue testing by bending which has yielded meaningful results leaves much to be desired since the precise location of the current collector grid within the plaque must be known before such results can be obtained. Consequently, it becomes necessary to select only appropriate test samples instead of random test samples, which, of course, is much more desirable.

It is therefore readily apparent that special equipment that can apply small and cyclic test loads to electrode plaque is required. It is essential in the production of more efficient batteries to provide a battery electrode stress or fatigue simulator which is capable of accurately reproducing the cyclic stresses incurred during battery operation.

SUMMARY OF THE INVENTION

The instant invention overcomes the problems encountered in the past by providing a battery electrode fatigue simulator which is capable of realistically obtaining the cyclic stresses incurred during battery operation and which is easily and readily adaptable for use in the testing of nickel electrode plaque.

The battery electrode fatigue simulator of this invention is made up of a support structure or frame which mounts therein a cam drive assembly, a pivotal "rocking" beam, an adjustable stationary beam, a suitable displacement measuring transducer or transducers and an appropriate ohmmeter or ohmmeters. Clamps are utilized to fixedly secure between the "rocking" beam and the stationary beam the electrode plaque which is to undergo simulated stress or fatigue substantially equivalent to that encountered during battery operation.

Any suitable drive means in the form of, for example, an electrical motor forms part of the cam drive assembly and is utilized to rotate a cam which in turn cyclically pivots the "rocking" beam in order to apply cyclic stress or fatigue to the electrode plaque. A determination of displacement versus resistance of the battery electrode plaque can be quickly and reliably established by this invention.

It is therefore relatively easy with the fatigue simulator of this invention to perform tests on substantially large numbers of manufacturing lots of battery electrodes or electrode plaque without subjecting the electrodes to actual use within a battery. Thereafter, an analysis of the results obtained with the battery electrode fatigue simulator of this invention can determine which manufacturing lot or, even more specifically, which electrodes will in fact provide maximum performance within the battery.

It is therefore an object of this invention to provide a battery electrode fatigue simulator which is capable of cyclically stressing battery electrodes or plaque in a manner representative of actual battery operating conditions.

It is another object of this invention to provide a battery electrode fatigue simulator which is insensitive to the location of the current collector grid within the plaque.

It is another object of this invention to provide a battery electrode fatique simulator which has the ability to prestrain the plaque.

It is a further object of this invention to provide a battery electrode fatigue simulator which is capable of fatiguing the plaque in tension.

It is still a further object of this invention to provide a battery electrode fatigue simulator which is economical to produce and which utilizes conventional, currently available components that lend themselves to standard mass producing manufacturing techniques.

For a better understanding of the present invention together with other and further objects thereof, reference is made to the following description taken in conjunction with the accompanying drawing and its scope will be pointed out in the appended claims.

DETAILED DESCRIPTION OF THE DRAWING

FIG. 2 is a side elevational view of the battery electrode fatigue simulator of this invention shown in partially segmented fashion; and FIG. 3 is a graphic representation of two characteristic resistance versus cycle curves obtained by the use of the battery electrode fatigue simulator of this invention.

DETAILED DESCRIPTION OF THE PREFERRED EMBODIMENT

Figure 1:
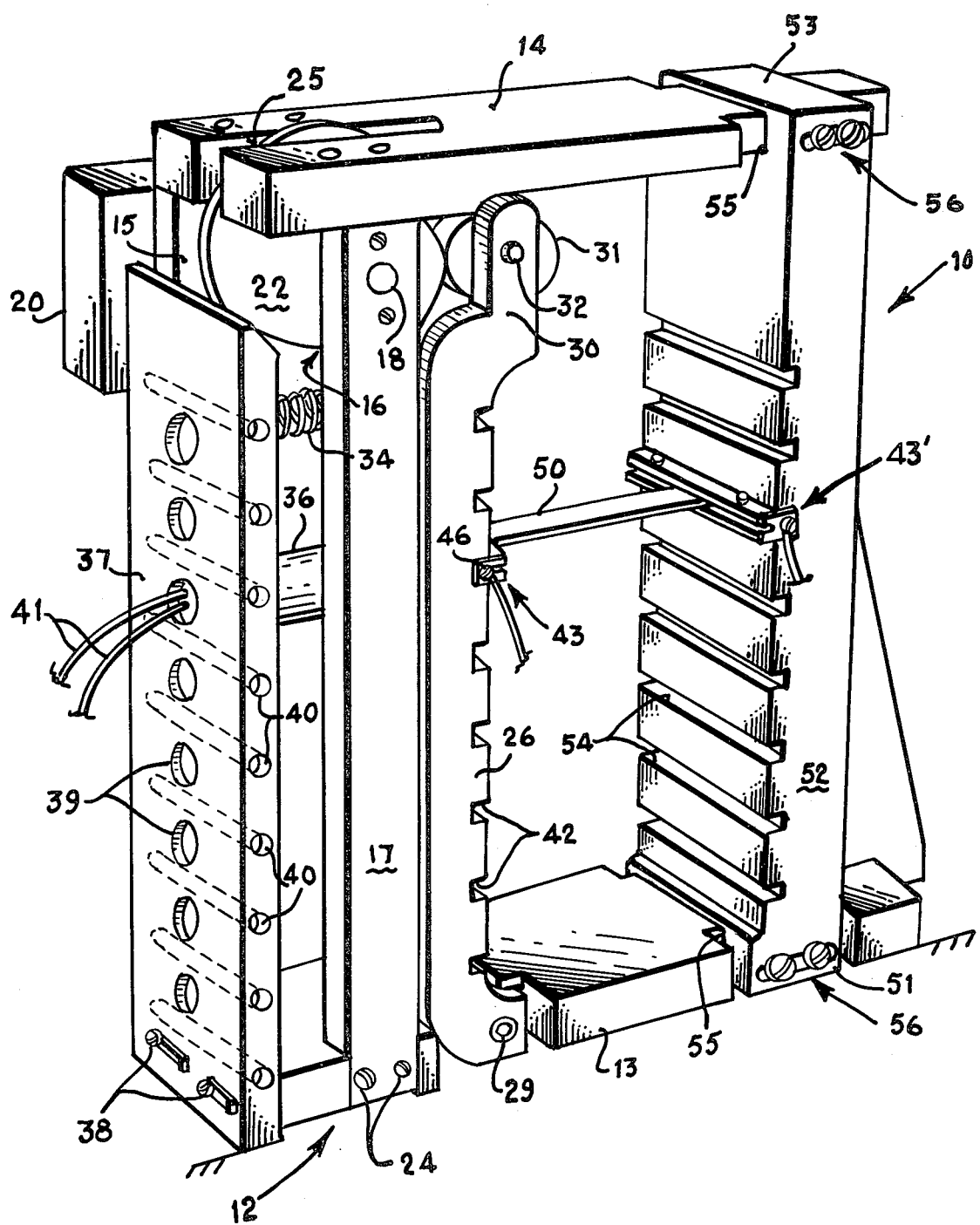
FIG. 1 is a pictorial representation of the battery electrode fatigue simulator of this invention.

It has been established that the mechanical fatigue characteristics of battery electrode plaque are related to the capacity retention characteristics of the active battery electrode. Therefore, before setting forth in detail the description of this invention it is necessary to clearly define the terms battery electrode and plaque. In general, the distinction between the electrode plaque and the active electrode is as follows: the electrode plaque is the electrode chemically inactive substrate in which the active chemical components are impregnated. In other words, a chemically impregnated plaque is an active battery electrode. In general, plaque consists of a sintered nickel sponge, that is typically 90% porous, in which there is an internal nickel current collection screen which is sintered to the sponge. It should, however, be realized that in conventional usage the terms electrode and plaque may be used interchangeably. Therefore, although the following description incorporates the proper usage of the terms, interchanging the terms electrode and plaque does not destroy the inventive concept set forth in detail hereinbelow.

Reference is now made to FIGS. 1 and 2 of the drawing which clearly illustrate the battery electrode fatigue simulator 10 of this invention. Fatigue simulator 10 is made up of a support structure or frame 12 having a base 13, a top support 14 and a back plate 15 which mounts therein a cam drive assembly 16. Cam drive assembly 16 is made up of an elongated support arm 17, a portion of back plate 15, a shaft 18, any suitable drive means in the form of, for example electric motor 20 and a cam 22 of a predetermined configuration. More specifically, arm 17 is supported at one end thereof to base 13 by any suitable securing means such as bolts 24. Rotatably supported between the other end of arm 17 and back plate 15 by shaft 18 is cam 22. Electric motor 20 is connected to cam 22 by means of shaft 18. In this manner, cam 22 can be rotated in a periodic fashion within frame 12 which includes a cut out portion 25 in top support 14 of the fatigue simulator 10 of this invention.

Situated adjacent cam drive assembly 14 is at a pivotally mounted "rocking" beam 26. Beam 26 is pivotally secured to base 13 of frame 12 at one end thereof by any suitable securing element in the form of a shaft and bearings 29. The other end of beam 26 has a split or bifurcated end 30 in which there is rotatably supported a follower in the form of roller 31. Roller 31 is freely rotatable on a shaft 32 located within end 30 of beam 26.

Any suitable biasing element in the form of, for example, a conventional compression spring 34 interconnected between a support peg 35 affixed to back plate 15 and "rocking" beam 26 maintains beam 26 in constant contact with cam 22. As shown in FIGS. 1 and 2 of the drawing spring 34 passes between support arm 17 and back plate 15. It should be noted, however, that the specifics of frame 12 and the biasing arrangement of this invention which includes spring 34 is not limited to that shown in the drawing as long as the concept involved is met, that is, for "rocking" beam 26 to have its roller 31 in a position to constantly engage cam 22. As cam 22 rotates, roller 31 follows along the curvature of the outer surface of cam 22 and will cyclically move in accordance therewith.

Any suitable displacement measuring device such as a conventional transducer 36 is interconnected between "rocking" beam 26 and a transducer bracket 37 made of any suitable material such as Plexiglas. Bracket 37 is fixedly mounted on base 13 and back plate 15 by means of conventional securing means such as bolts 38 or may form an integral part thereof, if desired. A plurality of apertures 39 are located in transducer bracket 37 so as to allow a single transducer 36 as shown or a plurality of transducers (not shown) to be secured therein by means of fastening elements located in transducer support guides 40. In addition, apertures 39 permit the transducer wires 41 to protrude therethrough. Wires 41 are connected to any suitable transducer data recording means (not shown).

Referring once again to "rocking" beam 26, beam 26 as a plurality of cutout portions or notches 42 formed therein. Notches 42 are positioned in substantial alignment with apertures 39 in transducer bracket 37 so as to enable a transducer 36 to be interconnected with that portion of beam 26 adjacent a corresponding notch 42.

Each notch 42 in beam 26 is capable of accepting therein a clamp 43 (one of which being shown in FIGS. 1 and 2 of the drawing). Each clamp 43 is removably secured within notch 42 by means of any suitable securing element in the form of, for example, bolt 44. In addition, clamp 43 has securing means therein, in the form of screw 46 so as to interconnect clamp 43 to one end of an ohmmeter 48. A set screw 49 located within clamp 43 is utilized to secure within clamp 43 any suitable element 50 which is to be fatigue tested in tension by the fatigue simulator 10 of this invention. Generally, element 50 takes the form of a battery electrode plaque.

Situated substantially parallel to "rocking" beam 28 is a stationary but adjustable beam 52 which appears to have the surface thereof a mirror image of the surface of beam 26. In other words, beam 52 has situated therein a plurality of notches 54 aligned with and oppositely disposed to notches 42 of beam 26. Both ends 51 and 53 of beam 52 may be adjustably mounted to base 13 and top support 14, respectively by having openings 55 therein which allow base 13 and top support 14 to pass therethrough. A conventional slot and bolt securing arrangement 56 located in ends 51 and 53 of beam 52 allows for adjustment of beam 52 to take place. In this manner, fatigue simulator 10 may be utilized with elements 50 of varying size. Furthermore, the adjustable feature allows a prestress to be applied to element 50, if desired. Any suitable material may be utilized to construct beams 26 and 52 as long as at least one of the beams is made of a nonconductive material.

Located within notch 54 of beam 52 is a clamp 43' which is identical to clamp 43 located within notch 42 of beam 26. Therefore, for purposes of simplicity and expendiency, a detailed description of claim 43' will be omitted, however, similar numerals will be utilized to identify elements of clamp 56 which are identical to clamp 43. The other end of ohmmeter 48 is interconnected to screw 46 of clamp 43'.

MODE OF OPERATION

Before testing operation of the battery electrode fatigue simulator 10 of this invention can commence, an electrode plaque 50 is clamped between beams 26 and 52. Thereafter, activation of motor 20 rotates cam 22 so as to "rock" or pivot beam 26. In this manner plaque 50 can be cyclically stressed by the rocking action of beam 26. It should be noted, however, that if desired a plurality of plaque 50 may be tested by providing additional clamps 43 and 43' in notches 42 and 54, respectively. In that case a separate transducer 36 may be associated with each plaque 50 tested or a single transducer 36 may be used with conventional mathematical computations applied in order to calculate the amount of movement of beam 26 for various positions along beam 26. Movement of cam 22 produces sufficient movement of beam 28 to stress in tension plaque 50. A prestress may also be applied to plaque 50 by means of appropriate adjustment of the position of beam 52 prior to the actual operation of this invention.

FIG. 3 is representative of two characteristic resistance versus cycle curves which may be obtained by the fatigue simulator 10 of this invention. The plaque 50 with the larger resistance increase (repesented by curve A) has poor fatigue characteristics while the other sample (represented by curve B) has excellent fatigue characteristics. In most instances the plaque samples would be taken from two different manufacturing lots. A manufacturing lot is generally a separate production run of a material and is so designated by the manufacturer by an identifying lot number.

Under normal test conditions a prestrain of $3.4 \times 10^{-3}$ and a cyclic strain of $8.5 \times 10^{-4}$ is applied by the fatigue simulator 10 of this invention. In most operations in order to compare the lot to lot fatigue characteristics, ten samples from each of four lots would be cycled 1000 times and the data statistically reduced. Resultant data would indicate significant differences in the degree of plaque breakup ($\Delta R/R$) and thus different capacity retention characteristics of the plaque when considering long cycle lives.

By the utilization of the battery electrode fatigue simulator 10 of this invention it is easy to identify those battery electrodes (plaque) which would in fact reduce performance of the battery associated therewith. In fact, it has been found that since the usual quality control procedures applied to plaque are not entirely adequate, it is even of greater importance to utilize the battery electrode fatigue simulator 10 of this invention in order to differentiate between various types of electrodes.

Stated more succinctly, the fatigue failure of the plaque is a result of the cyclic mechanical stresses, and these stresses can be correlated to the number of charge/discharge cycles of a battery. Therefore, improved cycle life can be obtained from nickel electrodes, for example, by building a fatigue-resistant plaque or by differentiating between those plaques which are in fact better fatigue resistant than others. The battery electrode fatigue simulator of this invention therefore is of a particular importance in the Ni-$H_2$ cells where the life-limiting component is the nickel electrode.

Although this invention has been described with reference to a particular embodiment it will be understood to those skilled in the art that this invention is also capable of further and other embodiments within the spirit and scope of the appended claims. For example, the fatigue simulator of this invention is not limited to the testing of electrode plaque but may be utilized in any instance wherein similar fatigue studies are to be undertaken.

We claim:

1. A battery electrode fatigue simulator comprising:
a frame;
a first support beam pivotally mounted at one end thereof to said frame and having a cam follower mounted at the other end thereof, said first support beam further having a plurality of notches situated therein, said notches being longitudinally displaced from each other with respect to the pivoting end of said first support beam, and means located in at least one of said notches for fixedly securing therein one end of an element which is to undergo fatigue simulation;
a second support beam adjustably secured at both ends thereof to said frame juxtaposed said first support beam, said second support beam having a plurality of notches therein oppositely disposed from said notches in said first support beam, and means located in at least one of said notches in said second support beam for fixedly securing the other end of said element therein;
a cam of preselected configuration rotatably mounted within said frame adjacent said cam follower, means operably connected to said cam for rotating said cam at a predetermined rate of speed, and means interconnected between said frame and said first support beam for constantly biasing said cam follower against said cam whereby rotational movement of said cam causes pivotal movement of said first support beam to take place in order to apply a predetermined cyclic stress to said element;
means secured to said frame juxtaposed said first support beam for determining the displacement of said first support beam at a plurality of locations along said first support beam, said locations being coincidental with said plurality of notches located in said first support beam in order to provide displacement information about said element during application of said cyclic stress; and
means operably connected between said element securing means in said first support beam and said element securing means in said second support beam for determining resistance in said element during the application of said cyclic stress;
whereby a relationship established between said displacement and said resistance is representative of battery electrode fatigue undergone during actual battery operation.

2. A battery electrode fatigue simulator as defined in claim 1 further comprising means situated in a plurality of said oppositely disposed notches for fixedly securing therebetween a plurality of elements, respectively, which are to undergo fatigue simulation.

3. A battery electrode fatigue simulator as defined in claim 1 wherein said resistance determining means comprises an ohmmeter.

4. A battery electrode fatigue simulator as defined in claim 3 wherein said displacement determining means is a transducer.

5. A battery electrode fatigue simulator as defined in claim 4 wherein said element is made up of electrode plaque.

6. A method of simulating the fatigue undergone by a plurality of electrodes during battery operation comprising the following steps:
(a) mounting a plurality of electrode plaques between a stationary support and a pivotal support, such that the plaques are longitudinally displaced from each other with respect to the pivoting end of said pivotal support;
(b) displacing said pivotal support in cyclic fashion in order to apply a cyclic stress in tension simultaneously to each of said electrode plaques;

(c) determining said cyclic displacement of said pivotal support during the application of said cyclic stress to said plaques;
(d) determining resistance in each of said plaques during application of said cyclic stress to said plaques; and
(e) establishing a relationship between said cyclic displacement and said resistance in each of said electrode plaques, said relationship being representative of battery electrode fatigue undergone during actual battery operation.

* * * * *